United States Patent
Ishimitsu (10) Patent No.: US 10,900,830 B2
(45) Date of Patent: Jan. 26, 2021

(54) OPTICAL HEAD AND MEASURING APPARATUS

(71) Applicant: ATONARP INC., Tokyo (JP)

(72) Inventor: Yoshiyuki Ishimitsu, Hachioji (JP)

(73) Assignee: ATONARP INC., Tokyo (JP)

( * ) Notice: Subject to any disclaimer, the term of this patent is extended or adjusted under 35 U.S.C. 154(b) by 0 days.

(21) Appl. No.: 16/493,103

(22) PCT Filed: Mar. 23, 2018

(86) PCT No.: PCT/JP2018/011683
§ 371 (c)(1),
(2) Date: Sep. 11, 2019

(87) PCT Pub. No.: WO2018/174244
PCT Pub. Date: Sep. 27, 2018

(65) Prior Publication Data
US 2020/0064187 A1    Feb. 27, 2020

(30) Foreign Application Priority Data

Mar. 23, 2017 (JP) ................. 2017-057297

(51) Int. Cl.
*G01J 3/44* (2006.01)
*G01J 3/02* (2006.01)
(Continued)

(52) U.S. Cl.
CPC .......... *G01J 3/0237* (2013.01); *G01J 3/0208* (2013.01); *G01J 3/0218* (2013.01); *G01J 3/10* (2013.01);
(Continued)

(58) Field of Classification Search
CPC ................. G01N 21/65; G01N 21/658; G01N 2021/656; G01J 3/44; G01J 3/02
(Continued)

(56) References Cited

U.S. PATENT DOCUMENTS 4,484,079 A  11/1984  Betz et al.
5,999,255 A  12/1999  Dupee et al.
(Continued)

FOREIGN PATENT DOCUMENTS

CN   201788152     4/2011
EP   1 403 675     6/2006
(Continued)

OTHER PUBLICATIONS

International Preliminary Report issued in corresponding International Application No. PCT/JP2018/011683, dated Oct. 3, 2019 (6 pages).
(Continued)

*Primary Examiner* — Md M Rahman
(74) *Attorney, Agent, or Firm* — Buchanan Ingersoll & Rooney PC (57) ABSTRACT

An optical head includes a first module that concentrates pump light and Stokes light on a first point; a second module that collects CARS light from the first point; and a third module that supports the first module and the second module. The first module includes: a high rigidity first frame; and a first optical system including a plurality of optical elements fixed to the first frame. The second module includes: a high rigidity second frame; and a second optical system including a plurality of optical elements fixed to the second frame. The third module includes a high rigidity third frame that fixes the first frame and the second frame.

18 Claims, 7 Drawing Sheets

(51) Int. Cl.
*G02B 6/42* (2006.01)
*G01J 3/10* (2006.01)

(52) U.S. Cl.
CPC .............. *G01J 3/44* (2013.01); *G02B 6/4226* (2013.01); *G01J 2003/104* (2013.01)

(58) Field of Classification Search
USPC .......................................................... 356/301
See application file for complete search history.

(56) References Cited

U.S. PATENT DOCUMENTS

| | | |
|---|---|---|
| 6,788,407 B1 | 9/2004 | Higdon |
| 2006/0050146 A1 | 3/2006 | Richardson |
| 2008/0081950 A1* | 4/2008 | Koenig .................. A61B 5/415 600/160 |
| 2010/0220315 A1 | 9/2010 | Morrell et al. |
| 2013/0003172 A1 | 1/2013 | Widzgowski |
| 2016/0157757 A1 | 6/2016 | Murthy |
| 2016/0216154 A1 | 7/2016 | Hofmeister et al. |
| 2016/0266362 A1 | 9/2016 | Kapanidis et al. |
| 2017/0018830 A1* | 1/2017 | Henry .................... G01R 27/32 |
| 2017/0059407 A1 | 3/2017 | Shiraiwa |
| 2018/0120155 A1* | 5/2018 | Rosen .................... G01N 21/01 |

FOREIGN PATENT DOCUMENTS

| | | |
|---|---|---|
| EP | 3 136 086 | 3/2017 |
| JP | 2009222531 A | 10/2009 |
| JP | 2016541027 A | 12/2016 |
| JP | 2017049043 A | 3/2017 |
| WO | 9845744 | 10/1998 |
| WO | 2015059682 A1 | 4/2015 |
| WO | 2016109877 | 7/2016 |
| WO | 2016123087 A2 | 8/2016 |

OTHER PUBLICATIONS

International Search Report (PCT/ISA/210) dated Jun. 26, 2018, by the Japan Patent Office as the International Searching Authority for International Application No. PCT/JP2018/011683.
Written Opinion (PCT/ISA/237) dated Jun. 26, 2018, by the Japan Patent Office as the International Searching Authority for International Application No. PCT/JP2018/011683.
European Search Report issued in corresponding European Patent Application No. 18772521, dated Nov. 19, 2020 (16 pages).
Douglas A. Greenhalgh et al., "The Application of Coherent Anti-Stokes Raman Scattering to Turbulent combustion Thermometry", Comubsion and Flame, Elsevier Science Publishing Co., Inc., vol. 49, No. 1-3, Jan. 1, 1983, pp. 171-181.

* cited by examiner

OPTICAL HEAD AND MEASURING APPARATUS

TECHNICAL FIELD

The present invention relates to an optical head and a measuring apparatus that is suitable for using nonlinear Raman spectroscopy.

BACKGROUND ART

Japanese Laid-open Patent Publication No. 2009-222531 discloses the provision of a light source apparatus for a nonlinear spectroscopy measurement system that has high performance but is simple, compact, and low cost. The disclosed light source apparatus is composed of a laser light source, which emits light pulses with a pulse width of 0.1 to 10 nanoseconds, and a photonic crystal fiber, which receives light pulses emitted from the laser light source and broadens the light pulses to generate and emit supercontinuum light. This apparatus uses the supercontinuum light emitted from the photonic crystal fiber to perform measurement according to nonlinear spectroscopy.

SUMMARY OF INVENTION

One application of Raman spectroscopy is observation of molecular distribution inside living cells and their dynamics without staining. Noninvasive measurement of the concentration of components, such as glucose, in blood using Raman spectroscopy is also being researched. The scattering cross-sectional area of Raman scattering is typically very small. This means that to obtain a favorable Raman spectrum from a measured object (measuring target), such as living cells or glucose in blood, an exposure time of several seconds to several minutes is required. Coherent Anti-Stokes Raman Scattering (hereinafter referred to as "CARS"), which is one form of nonlinear Raman spectroscopy, is capable of amplifying weak Raman signals and obtaining Raman images at high speed. The CARS process usually requires two light pulses of different wavelengths (called "pump light" and "Stokes light"), and when the frequency difference of the light pulses matches the molecular vibration, very intense CARS light is generated.

As a method of obtaining CARS light, a method (called "multicolor CARS spectroscopy" or "multiplex CARS spectroscopy") that spectrally detects generated CARS light using a broadband light source as the Stokes light is known. With this method, since the Raman spectrum can be estimated from the spectrum of CARS light, more information can be acquired than with a method that detects only a specified spectrum component, which means more information can be acquired in a short time. One way to obtain broadband Stokes light is to use a phenomenon whereby broadband light (called "supercontinuum light") is internally generated when laser light is introduced into an optical fiber such as a photonic crystal fiber (PCF). After the supercontinuum light exits the PCF, only components with a wavelength that is longer than the pump light (excitation light) are extracted using a long pass filter, the extracted components are used as the Stokes light, are combined with the pump light using a dichroic mirror or the like, and are emitted so as to be concentrated or focused on a measurement object (measurement target, sample). The CARS light generated at the measurement target is guided to a spectrometer to measure (detect) the spectrum.

With CARS spectroscopy, it is necessary to precisely match the optical axis positions and angles of the pump light and the Stokes light emitted onto the sample. Any deviation here can cause a drop in the generation efficiency of CARS light. For this reason, in a system, such as a CARS microscope, that uses CARS spectroscopy, the plurality of optical elements that construct the optical paths of pump light, Stokes light, and CARS light are disposed on a large and stable stage, and the positions of these optical elements are subjected to fine control. This has prevented a system that is suitable for using CARS spectroscopy but is handy and can be carried anywhere and is compact to the extent that it can be worn on the body and incorporated in a wearable device from being provided.

One aspect of the present invention is an optical head including: a first module that concentrates (focuses) a plurality of light of different frequencies or frequency bands, for example, pump light and Stokes light used in CARS, on a first point to obtain a nonlinear Raman effect; a second module that collects light to be measured (measuring light, measurement light), for example, CARS light, emitted from the first point; and a third module that supports the first module and the second module. The first module includes a high rigidity first frame and a first optical system that includes a plurality of optical elements fixed to the first frame. The second module includes a high rigidity second frame and a second optical system that includes a plurality of optical elements fixed to the second frame. The third module includes a high rigidity third frame that fixes the first frame and the second frame.

In this optical head, out of the large number of optical elements that construct a nonlinear Raman spectroscopy optical system, the plurality of optical elements for concentrating a plurality of light of different frequencies or frequency bands, such as pump light and Stokes light, on a first point can be fixed to and integrated with a highly rigid first frame. The plurality of optical elements for collecting light to be measured can be fixed to and integrated with a highly rigid second frame that differs to the first frame. This means that it is possible to integrate and positionally adjust the concentrating or focusing optical elements and the collecting optical elements respectively by fixing to separate frames, which makes it possible to provide an optical head that is compact and is capable of precisely concentrating a plurality of light for obtaining a nonlinear Raman effect on a predetermined point.

The first module may include a mechanism that adjusts (finely adjusts) and then fixes an attachment position of at least one optical element included in the first optical system to the first frame, so that when attaching to the first frame, it is possible to perform focusing adjustment (adjustment of the concentrating position) of the plurality of light. In the same way, the second module may include a mechanism that adjusts (finely adjusts) and then fixes an attachment position of at least one optical element included in the second optical system to the second frame.

In the first module, the first frame may include a region that extends in two dimensions and the plurality of optical elements included in the first optical system may be laid out in two dimensions in the first frame. This facilitates attachment and position adjustment of the optical elements. In the same way, the second frame may include a region that extends in two dimensions and the plurality of optical elements included in the second optical system may be laid out in two dimensions in the second frame.

The first optical system may include a plurality of optical elements that adjust the focus of the plurality of light. This makes it possible to correct chromatic aberration of the plurality of light of different wavelengths using different optical elements. When supercontinuum light is used as the Stokes light, it is possible to improve the light intensity at the focusing point of the pump light relative to the Stokes light, which tends to reduce noise in the CARS light.

The optical head may further include a first laser light supplying unit and a second laser light supplying unit that are fixed to the first frame and each supply at least one of the plurality of light, and the plurality of optical elements of the first optical system may include a plurality of optical elements that construct an optical path that guides first laser light supplied from the first laser light supplying unit and second laser light supplied from the second laser light supplying unit to a shared first objective lens that irradiates the first point. In addition, the optical head may include a first XY position adjustment unit that adjusts (finely adjusts) a position in two dimensions, which are perpendicular to an optical axis of the first laser light, of the first laser light supplying unit relative to the first frame and a second XY position adjustment unit that adjusts (finely adjusts) a position in two dimensions, which are perpendicular to an optical axis, of the second laser light, of the second laser light supplying unit relative to the first frame. This makes it possible to perform position adjustments, relative to the first frame, in the XY directions of the optical axes of the plurality of light respectively for obtaining the nonlinear Raman effect.

The optical head may further include: a first collimator lens that converts the first laser light to parallel light; a second collimator lens that converts the second laser light to parallel light; a first Z position adjustment unit that adjusts (finely adjusts) a position, in the optical axis direction of the first laser light, of the first collimator lens relative to the first frame; and a second Z position adjustment unit that adjusts (finely adjusts) a position, in the optical axis direction of the second laser light, of the second collimator lens relative to the first frame. The first Z position adjustment unit may be fixed to the first frame together with the first laser light supplying unit via the first XY position adjustment unit, and the second Z position adjustment unit may be fixed to the first frame together with the second laser light supplying unit via the second XY position adjustment unit. It is possible to adjust the positions of the plurality of light and collimator lenses respectively for obtaining a nonlinear Raman effect relative to the first frame. In addition, by fixing the Z position adjustment unit to the first frame via the XY position adjustment unit, it is possible to perform Z position adjustment of the respective laser light supplying units in units of the laser light supplying units before fixing via the XY position adjustment unit to the first frame. The respective laser light supplying units may include units that adjust (finely adjust) the position in two dimensions perpendicular to the optical axes of the laser light relative to the collimator lenses, and it may be possible to perform position adjustments in the XY direction of the laser light relative to the collimator lenses in advance.

The respective laser light supplying units may each include a laser element that supplies the laser light or a connector that connects to an optical fiber that supplies the laser light, and position adjustment of a collimator lens and a laser element or a connector for connecting to an optical fiber may be performed in units of the laser light supplying units before fixing to a first frame.

The optical head may include a fourth module in which a sample is fixed to the first point. The fourth module includes a high rigidity fourth frame that is fixed to the third frame and a sample holder that is fixed to the fourth frame, which makes it possible to precisely fix the position of the sample holder relative to the first optical system and the second optical system via the third frame, the first frame, and the second frame. The fourth module may include a mechanism that adjusts (finely adjusts) and then fixes the orientation of the sample holder.

The plurality of optical elements of the second optical system may include a plurality of optical elements that construct an optical path from a second objective lens that concentrates the light to be measured to a light receiving unit that receives the light to be measured. The optical head may include: a third XY position adjusting unit that adjusts (finely adjusts) a position in two dimensions, which are perpendicular to an optical axis of light of the measured object, of the light receiving unit relative to the second frame; and a focus adjusting unit that adjusts (finely adjusts) a position, in an optical axis direction of the light to be measured, of the second objective lens relative to the second frame. In the second optical system that collects the light to be measured from a measured object (sample), by adjusting (finely adjusting) the positions of the optical elements in the XY directions that are perpendicular to the optical axis and in the Z direction that is parallel to the optical axis, it is possible to efficiently detect the light to be measured. The light receiving unit may be a detector itself that detects the light to be measured or may be a third connector that connects to a third optical fiber that guides the light to be measured to a detector. The light to be measured may include light that has been generated due to at least one of stimulated Raman scattering and coherent anti-Stokes Raman scattering.

Another aspect of the present invention is a measuring apparatus (measurement device) including: the optical head described above; a light source unit that outputs the plurality of light; and a detector that detects light to be measured.

DESCRIPTION OF EMBODIMENTS

Coherent anti-Stokes Raman scattering (or "CARS") spectroscopy, stimulated Raman scattering (or "SRS") spectroscopy, and the like are known as methods of nonlinear Raman spectroscopy, one type of Raman spectroscopy. The present invention is described below by way of an example apparatus that uses CARS spectroscopy.

Figure 1:
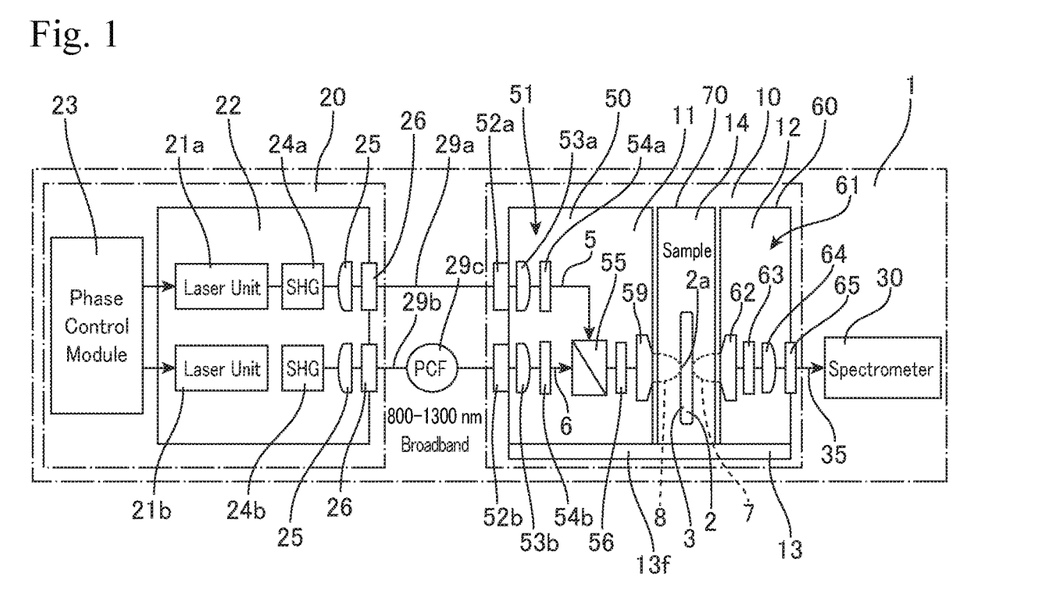
FIG. 1 is a block diagram depicting the overall configuration of a measuring apparatus.

FIG. 1 is a block diagram depicting the configuration of a measuring apparatus (measurement device) 1 that measures a component, for example, blood sugar level, of a sample, such as blood, stored in a cuvette, as an example of a measuring apparatus that uses CARS spectroscopy. The measuring apparatus 1 includes: an optical head 10 that emits first light (first laser light, first laser beam, pump light) 5 and second light (second laser light, second laser beam, Stokes light) 6, out of a plurality of types of light for obtaining a nonlinear Raman effect, onto a sample 3 stored in a cuvette 2 and collects CARS light 7, which is the light to be measured and is emitted from the sample 3; a light source unit 20 that serves as a light source for the pump light 5 and the Stokes light 6; and a detector (spectrometer) 30 that detects the collected CARS light 7. The light source of the measuring apparatus 1 is a laser beam, and the light source unit 20 includes a laser module 22, which includes two laser units 21a and 21b that respectively output laser pulses, and a phase control module (phase adjustable clock module, phase adjustable dual clock) 23 that controls the phases of the pulses outputted from the laser units 21a and 21b.

One example of the laser module 22 is a dual-color laser source (DCLS) that uses a semiconductor laser or lasers as a light source or sources. The laser module 22 has a peak power at a kilowatt level at a wavelength of 1550 nm, and includes, as the laser units 21a and 21b, small master oscillator power amplifier (MOPA)-type fiber lasers (MOPA fiber lasers) that are capable of outputting a pulse laser of several nm, with an example pulse width of 3 to 5 ns at several hundred kHz, for example, 100 to 500 kHz. The laser module 22 further includes second harmonic generators (SHGs) 24a and 24b that double the laser frequencies of the laser units 21a and 21b to output lasers with a wavelength of 775 nm, and lenses 25 and connectors 26 for coupling with optical fibers (fiber cables) 29a and 29b. Using the laser module 22, it is possible to obtain two sets of laser pulses, which have a wavelength of 775 to 780 nm and a level of several hundred watts, for example, 200 to 400 W with a pulse width of 3 to 5 ns and whose relative phase can be controlled.

One set of laser pulses are supplied as pump light 5 to the optical head 10 via the optical fiber 29a. The other set of laser pulses are supplied as the Stokes light 6 to the optical head 10 via the optical fiber 29b and a photonic crystal fiber (PCF) 29c. The Stokes light 6 that reaches the optical head 10 is whitened light (broadband light, supercontinuum light, SC light) with a wavelength of around 800 to 1300 nm. Note that these wavelengths and wavelength bands of the pump light 5 and the Stokes light 6 are mere examples, and although a desired wavelength is obtained in the present embodiment by an SHG using the fiber laser with an oscillation wavelength of around 1500 nm as the laser light source, a fiber laser of around 1000 to 1100 nm may be used as the light source, the light may be used without passing through a SHG, or a solid state laser such as a titanium sapphire laser may be used as the light source. The fiber 29a that transmits the pump light 5 may be a low-loss polarization maintaining fiber (PMF), and the time difference relative to the Stokes light 6 that passes through the PCF 29c may be controlled by adjusting the length of the fiber 29a.

Figure 2:
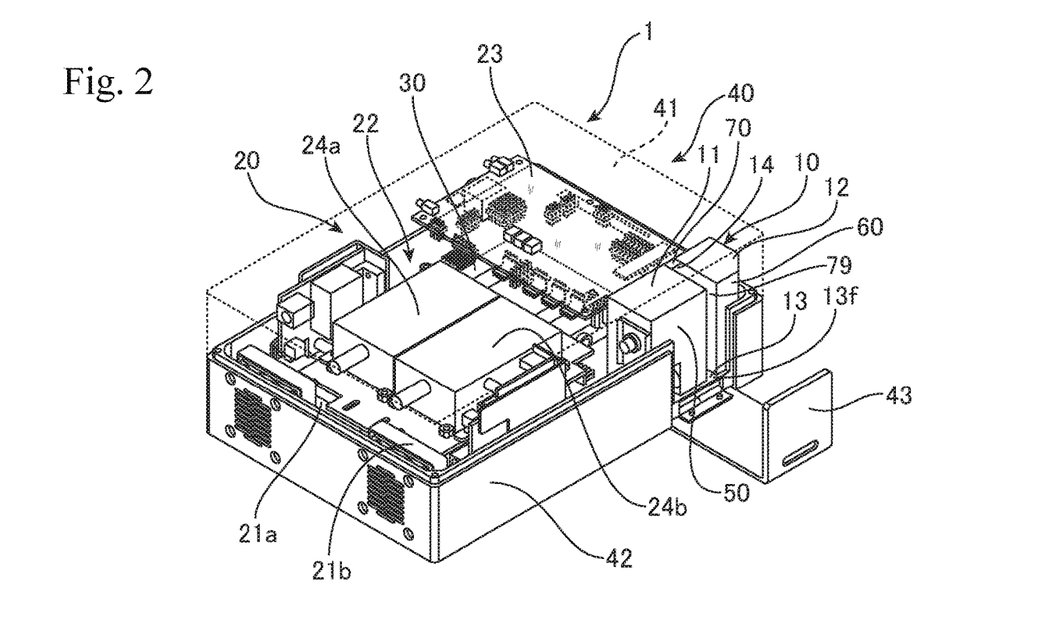
FIG. 2 is a perspective view depicting an internal layout of the measuring apparatus.

FIG. 2 depicts the internal layout of the measuring apparatus 1 with the upper housing removed. This measuring apparatus 1 has a compact form realized by disposing the laser units 21a and 21b and the SHGs 24a and 24b on two levels (two layers arrangement), and is enclosed in a handy type housing 40 with an overall size of 230 mm×160 mm×75 mm, which is smaller than B5 size. The housing 40 includes an upper housing 41, a lower housing 42, and an opening/closing door 43 for inserting and removing the cuvette 2 as a sample into and out of the optical head 10. The drawing depicts a state where the upper housing 41 is removed.

The optical head 10 is in the form of a box or block with an overall size of around 72 mm×30 mm×20 mm. The optical head 10 includes a first module (emission block) 11 that concentrates the pump light 5 and the Stokes light 6 at a first point 2a of the cuvette 2, a fourth module (sample holding block) 14 that holds the cuvette 2 containing the sample at the first point 2a, a second module (collection block) 12 that collects the CARS light 7 from the first point 2a, and a third module (supporting block) 13 that supports the first module 11 and the second module 12.

The first module 11 includes a highly rigid (high rigidity) first frame 50 and a first optical system 51 including a plurality of optical elements that are fixed to the first frame 50. The first frame 50 is a shielding-type frame and functions as a housing that blocks light to be a shading type. This prevents leaking light from locations aside from an objective lens 59 from becoming incident on the fourth module 14 on the sampling side. The second module 12 includes a highly rigid (high rigidity) second frame 60 and a second optical system 61 including a plurality of optical elements that are fixed to the second frame 60. The second frame 60 too is a shielding-type frame and functions as a housing that blocks light to be a shading type. This makes it possible to shield light from locations aside from the fourth module 14 on the sampling side acquired through the objective lens 62.

The fourth module 14 includes a highly rigid (high rigidity) fourth frame 70. The cuvette 2 including the sample for which CARS light 7 is to be collected is fixed to the fourth frame 70 at the first point 2a. The third module 13 includes a highly rigid (high rigidity) third frame 13f, and by fixing the first frame 50, the second frame 60, and the fourth frame 70 to the third frame 13f, the optical elements of the first optical system 51, which is the illumination optical system, and the optical elements of the second optical system 61, which is the collection optical system, can be precisely positioned relative to the first point 2a of the cuvette 2 that contains the sample.

Examples of a lightweight, highly rigid frame include a frame made of aluminum, aluminum alloy, or stainless steel. There are also composite materials in which metals, such as MMC (Metal Matrix Composites) and ceramics are combined as materials that have an even lower coefficient of thermal expansion, higher rigidity, and a lower weight. For this highly rigid frame, as one example, the Young's modulus (GPa) may be 60 or higher, 70 or higher, 100 or higher, or even 130 or higher. The thermal expansion coefficient (linear expansion coefficient, $10^{-6}$/K) may be 25 or lower, 20 or lower, 15 or lower, or even 10 or lower.

In the optical head 10, the first to fourth frames 50, 60, 13f, and 70 also function as shielding blocks, and when the first to fourth modules 11, 12, 13 and 14 are combined, parts aside from an opening 79 where the cuvette 2 is inserted are shielded from external light. By disposing the optical head 10 in the housing 40 with the opening 79 facing the opening/closing door 43, it is possible to prevent leaking light from other equipment housed in the housing 40 and the air vents or the like of the housing 40 from reaching the cuvette 2. The opening/closing door 43 itself also shields against light, and by closing the opening/closing door 43, external light can be blocked, so that the cuvette 2 is irradiated with only the pump light 5 and the Stokes light 6 supplied from the first module 11, and at the second module 12, only the CARS light 7 emitted from the cuvette 2 is collected.

A first optical system 51 housed in the first module 11 is an illumination optical system and includes a plurality of optical elements that construct optical paths to the shared first objective lens 59, which irradiates the first point 2*a* with the pump light 5 and the Stokes light 6, from a first connector (first laser light supplying unit, first laser beam supplying unit) 52*a* for connecting to the first optical fiber 29*a* that supplies the pump light 5 and a second connector (second laser light supplying unit, second laser beam supplying unit) 52*b* for connecting to the second optical fiber 29*b* that supplies the Stokes light 6. More specifically, the first optical system 51 includes a first collimator lens 53*a* that converts the pump light 5 introduced via the first connector 52*a* into parallel light, a band pass filter (narrow band pass filter) 54*a* that narrows the bandwidth of the pump light 5, and a dichroic mirror (or dichroic prism) 55 that combines the pump light 5 and the Stokes light 6 to make the light coaxial. The first optical system 51 further includes a second collimator lens 53*b* that converts the Stokes light 6 introduced via the second connector 52*b* into parallel light, and a long wavelength pass filter 54*b* that blocks the short wavelength-side spectral components of the Stokes light 6 that is SC light. The Stokes light 6 that has passed through the long wavelength pass filter 54*b* is combined with the pump light 5 by the dichroic mirror 55 and coaxially introduced into the objective lens 59 via a notch filter 56. These optical elements, including connectors, lenses and filters, are fixed so as to not move relative to the first frame 50 during normal operation.

The objective lens 59 that focuses the pump light 5 and the Stokes light 6 that have been coaxially combined on a predetermined point (first point) 2*a* of the cuvette 2 has a high NA, which eases the phase matching conditions for the pump light 5 and the Stokes light 6. In addition, in the present embodiment, chromatic aberration is improved by using cemented lenses for the collimator lens 53*b*, which collimates the Stokes light 6 that is light of a wide band, and for the objective lens 59, which concentrates (focuses) light produced by combining the pump light 5 and the Stokes light 6.

The second optical system 61 housed in the second module 12 includes a plurality of optical elements that construct an optical path from the second objective lens 62, which collects and concentrates the CARS light 7 from the first point 2*a*, to a third connector (light receiving unit) 65 that connects to the third optical fiber 35 that outputs the CARS light 7 to the spectrometer 30. More specifically, the second optical system 61 includes the objective lens (collecting lens) 62, the notch filter 63 for removing noise from the concentrated light, and a collimator lens 64 that concentrates the CARS light 7 collected by the objective lens 62 into the third connector 65. In this system 61, a cemented lens is used as the collimator lens 64 to correct chromatic aberration. These optical elements, including connectors, lenses, and filters, are fixed so as to not move relative to the second frame 60 during normal operation.

Figure 3:
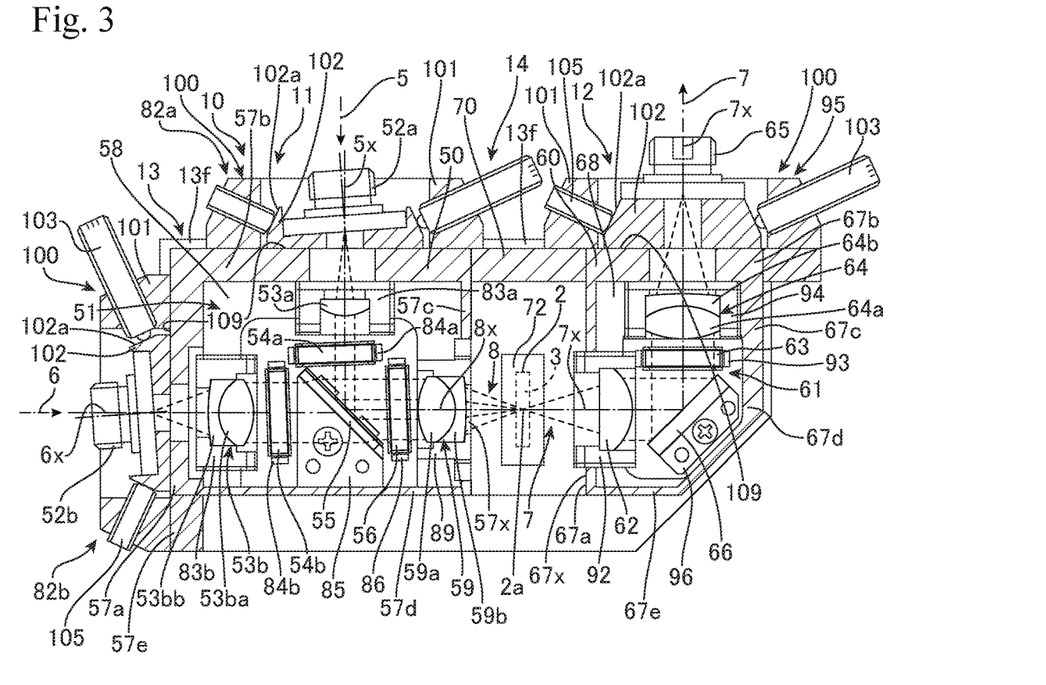
FIG. 3 is a plan view depicting the configuration of an optical head.
Figure 4:
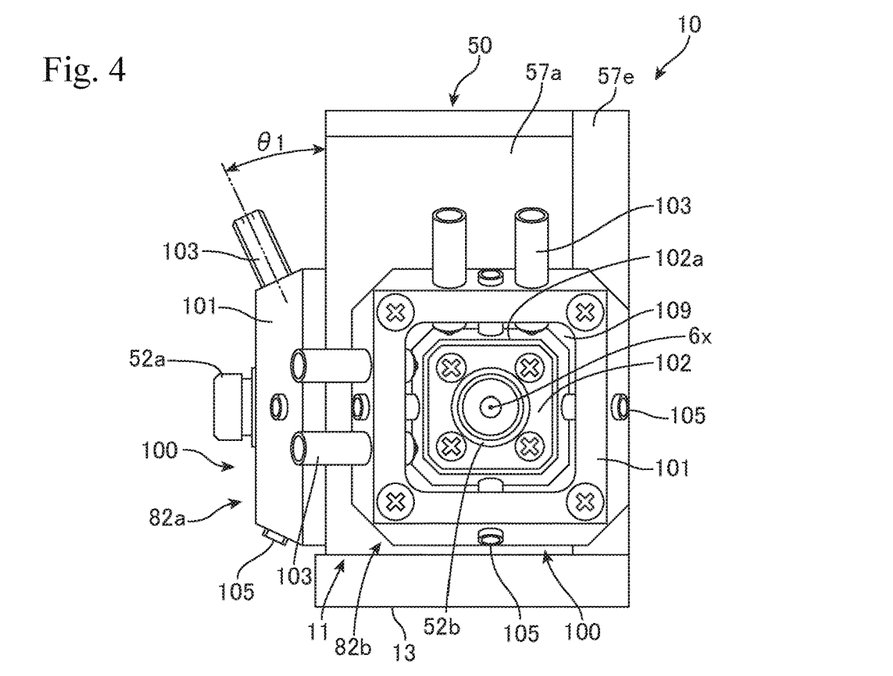
FIG. 4 is a side view of the optical head shown in FIG. 3.

A more detailed configuration of the optical head 10 is depicted in FIG. 3. FIG. 4 depicts the external appearance of the optical head 10 when looking from the side (the direction in which the Stokes light 6 is incident). The optical head 10 includes the emission block (first module) 11, the sample holding block (fourth module) 14, the collection block (second module) 12, and the supporting block (third module) 13 that supports the other blocks. The blocks 11, 14 and 12 are linearly arranged (mounted) on the supporting block 13 in the described order. The respective blocks 11, 14 and 12 include the high rigidity first frame 50, fourth frame 70, and second frame 60 that are each fixed to the high rigidity frame (third frame, shared frame) 13*f* of the supporting block (shared base) 13.

The first frame 50 that constructs the emission block 11 is a rectangular box, and internally includes a storage region (base plate) 58 for optical elements and extends in two dimensions and is surrounded by walls 57*a* to 57*d* in four directions. The second connector 52*b* for connecting the second optical fiber 29*b* that introduces the Stokes light 6 is fixed to one side wall 57*a* of the first frame 50, and the first connector 52*a* for connecting the first optical fiber 29*a* that introduces the pump light 5 is fixed to the side wall 57*b* that is adjacent to the side wall 57*a*. A window (opening, aperture) 57*x* for illuminating the cuvette 2 with the pump light 5 and the Stokes light 6 is provided on the side wall 57*c*, which is adjacent to the side wall 57*b* and faces the sample holding block 14. Accordingly, three of the side walls 57*a* to 57*c* out of the four side walls 57*a* to 57*d* of the rectangular first frame 50 are used for inputting and outputting light, and the remaining side wall 57*d* faces the side wall of the housing 40 when the emission block 11 is housed in the housing 40 and is a wall for shielding the inside of the emission block 11.

The optical elements are disposed in a region 58 that extends in two dimensions inside the first frame 50 so as to form optical paths in three perpendicular directions that are centered on the dichroic mirror 55. One of the optical paths includes a second connector 52*b*, a second collimator lens 53*b*, and a filter 54*b* for guiding the Stokes light 6 to the dichroic mirror 55, another one of the optical paths includes a first connector 52*a*, a first collimator lens 53*a*, and the filter 54*a* for guiding the pump light 5 to the dichroic mirror 55, and yet another one of the optical paths includes a filter 56, an objective lens 59, and an illumination window 57*x* for guiding the light combined by the dichroic mirror 55 to the first point 2*a*. Each optical element is provided with an anti-reflection film, the connectors 52*a* and 52*b* also have their connection angles adjusted relative to the optical axes in accordance with an angled physical contact (APC) connection method to suppress back reflection. The filters 54*a*, 54*b*, and 56 are also disposed at appropriate angles to the optical axes to suppress back reflection.

The emission block 11 further includes a mechanism for finely adjusting and then fixing the attachment positions on the first frame 50 of the optical elements included in the first optical system 51 disposed on the inside and the wall surfaces of the first frame 50, with the side walls of the first frame 50 and the storage region 58 that extends in two dimensions as a base. In more detail, the emission block 11 includes: a first XY table (first XY position adjustment unit) 82*a* that finely adjusts and then fixes a position relative to the first frame 50, in the present embodiment, the wall surface 57*b*, of the first connector 52*a* that introduces the pump light 5 in two dimensions (XY directions) perpendicular to the optical axis 5*x* of the pump light 5; a second XY table (second XY position adjustment unit) 82*b* that finely adjusts and then fixes a position relative to the first frame 50, in the present embodiment, the wall surface 57*a* and an extended wall 57*e*, of the second connector 52*b* that introduces the Stokes light 6 in two dimensions perpendicular to the optical axis 6*x* of the Stokes light 6; and a holder (focus adjustment unit) 89 that slides the first objective lens 59 that emits the emitted light (emitted beam, outgoing light) 8 produced by combining the pump light 5 and the Stokes light 6 in (along with) the optical axis 8x direction (Z direction) of the emitted beam 8 and finely adjusts and then fixes the position relative to the first frame 50, in the present embodiment the wall surface 57c.

One example of the focus adjustment unit 89 moves the objective lens 59 in and out in the axis 8x direction by rotating an inner frame, which includes the objective lens 59 and is screwed onto an outer frame that is fixed to the first frame 50. The focus adjustment unit 89 may be a mechanism that fixes the inner frame to the outer frame using a plurality of screws and controls the position of the lens along the optical axis and the angle by tightening and loosening the screws, or may be a mechanism that moves the objective lens 59 on a rail fixed to the first frame 50.

The first XY table 82a and the second XY table 82b are fine adjustment tables 100 with a same configuration for moving and fixing the connectors 52a and 52b in two dimensions across the wall surfaces. One example of the fine adjustment table 100 is a structure provided with an inclined surface and adjustment screws as depicted in FIGS. 3 and 4. The fine adjustment table 100 that fixes the connector 52b will now be described as an example. The fine adjustment table 100 includes an inner frame 102 with a rectangular outer circumference to which the connector 52b to be moved is fixed and an outer frame 101 provided with a rectangular inner circumference that surrounds the periphery of the inner frame 102. The outer frame 101 is fixed to the wall surface 57a of the first frame 50 by screws or the like, and a wall surface 109 that is perpendicular to the optical axis 6x is provided on the inside. The inner frame 102 moves in close contact with the surface (wall surface) 109 perpendicular to the optical axis 6x.

Around the outer circumference (the four edges) on four sides, the inner frame 102 includes tapered surfaces (pressing surfaces) 102a that extend outward toward the wall surfaces 109. The outer frame 101 includes position adjustment screws 103 which come into contact with the pressing surfaces 102a in directions that are substantially perpendicular, and fixing screws 105. An angle θ1 between the screws 103 and 105 and the wall surface 109 is 10 to 30 degrees, for example, but may be 15 to 25 degrees. The fixing screws 105 are respectively disposed in the centers of the four tapered edges 102a on the four sides of the inner frame 102, and by tightening the fixing screws 105, the inner frame 102 can be fixed in a state where the inner frame 102 is pressed onto the wall surface 109, that is, where the connector 52b is in close contact with the wall surface 57a.

Two position adjustment screws 103 are disposed on each of two adjacent tapered surfaces 102a, with the fixing screws 105 disposed in between. Accordingly, by moving the position adjusting screws 103 in and out relative to the outer frame 100 (that is, tightening and loosening the screws), the position of the inner frame 102 can be moved in two dimensions (the XY directions) relative to the outer frame 100. In addition, the orientation of the inner frame 102 can be finely adjusted around the optical axis 6x by adjusting the inserted depth of the adjustment screws 103 located on both sides of the fixing screws 105. Accordingly, the fine adjustment table 100 functions as an XYθ table that is capable of adjusting the two-dimensional (XY direction) position and the angle around the optical axis of the inner frame 102 relative to the wall surface 109 that serves as the base. By loosening the fixing screws 105, finely adjusting the position of the inner frame 102 relative to the outer frame 101 using the position adjusting screws 103, and then tightening the fixing screws 105, the position of the connector 52b relative to the first frame 50 can be finely adjusted and then fixed.

The emission block 11 further includes a holder (first Z position adjustment unit) 83a that supports the first collimator lens 53a, which converts the pump light 5 to parallel light, so that the first collimator lens 53a slides relative to the first frame 50 in the optical axis 5x direction (Z-axis direction) of the pump light 5. The holder (first Z position adjustment unit) 83a can be fixed after finely adjusting the attachment position relative to the first frame 50. The emission block 11 also includes a holder (second Z position adjustment unit) 83b that slides the second collimator lens 53b, which converts the Stokes light 6 into parallel light, relative to the first frame 50 in the optical axis 6x direction and can be fixed after finely adjusting the attachment position. As the mechanisms of the holders 83a and 83b, it is possible to use the same mechanism as the holder (focus adjustment unit) 89.

The emission block 11 may further include holders 84a and 84b that slidably support the attachment positions of other optical elements, for example the filters 54a and 54b, relative to the first frame 50 and are capable of finely adjusting and then fixing the attachment positions. In the same way, the emission block 11 may include a holder 85 that is capable of finely adjusting and then fixing the attachment position and angle of the dichroic mirror 55 and a holder 86 that is capable of finely adjusting and then fixing the attachment position of the filter 56.

The holder (focus adjustment unit) 89 is capable of finely adjusting the position in the optical axis 8x direction of the objective lens 59, which has overall positive refractive power and includes a biconvex positive lens 59a and a negative meniscus lens 59b that is convex on the emission side and is cemented to the emission side of the positive lens 59a. By adjusting the position of the objective lens 59 in the optical axis 8x direction, it is possible to finely adjust the overall focal position (i.e., to perform focusing) of the emitted light (output light) 8 produced by combining the pump light 5 and the Stokes light 6 that have been adjusted so as to be coaxially emitted through fine adjustment of the position and angle of the dichroic mirror 55. The focal position (i.e., focusing) of the pump light 5 included in the emitted light 8 can be independently finely adjusted by finely adjusting the attachment position in the optical axis 5x direction of the collimator lens 53a, which has positive refractive power and is convex on the emission side, using the holder 83a. The focal position (i.e., focusing) of the Stokes light 6 included in the emitted light 8 can be independently finely adjusted by finely adjusting the position in the optical axis 6x direction of the collimator lens 53, which has overall positive refractive power and is composed of a positive biconvex lens 53ba and a negative meniscus lens 53bb that is convex on the incident side and is cemented to the incident side of the biconvex lens 53ba, using the holder 83b. It is difficult to make the light flux completely parallel at the collimator lenses 53a and 53b, so that by adjusting the positions of the collimator lenses 53a and 53b, it is possible to separately adjust the focal positions of the pump light 5 and the Stokes light 6.

Also, in addition to these position adjustments in each optical axis direction (Z direction), the emission block 11 is capable of finely adjusting the positions of the connectors 52a and 52b, which receive the pump light 5 and the Stokes light 6, in the XY directions that are perpendicular to the optical axes 5x and 6x using the XY tables 82a and 82b. Accordingly, in the emission block 11, the positions of the optical path of the pump light 5 and the optical path of the Stokes light 6 can be controlled in all of the XY directions, which are perpendicular to the optical axes 5x and 6x respectively, and the Z directions, which are parallel to the optical axes 5x and 6x respectively.

That is, in the emission block 11, the position in the XY directions that are perpendicular to the optical axis 8x of the focal point of the pump light 5 included in the emitted light 8 and the position in the XY directions that are perpendicular to the optical axis 8x of the focal point of the Stokes light 6 can be controlled independently. This means that at the emission block 11, the position of the pump light 5 in the XYZ directions that are perpendicular and parallel to the optical axis 8x of the focal point at the focusing position 2a in the sample 3 held in the cuvette 2 and the position in XYZ directions of the Stokes light 6 can be controlled independently, and the focal point of the pump light 5 and the focal point of the Stokes light 6 can be precisely aligned with the focusing position 2a. Accordingly, it is possible to efficiently generate the CARS light 7 and it is possible to obtain CARS light 7 that is sufficiently intense for measurement even when a laser light source with a low output is used.

Provided that CARS light 7 of sufficient intensity can be obtained, it is desirable for the intensity of the laser beam emitted onto the sample 3 to be low. This is because it becomes possible to perform measurement without causing variation in the state, as examples, the temperature, concentration, and the like, of the sample 3. In particular, when the measuring apparatus 1 is a system for irradiating the human body with laser beam to obtain the CARS light 7 in applications such as measuring glucose inside capillaries (blood vessels) of the body, it is desirable for the pump light 5 and the Stokes light 6 used to irradiate the body to have energy of a level that does not affect the human body. In the measuring apparatus 1 according to the present embodiment, it is possible to control the respective focal positions of the pump light 5 and the Stokes light 6 with high precision and suppress errors in the focal points of the light at the focusing position 2a, which make it possible to obtain CARS light 7 with a high output using a low energy laser.

In the emission block 11, the lenses 53a, 53b, and 59, the filters 54a, 54b, and 56, and the dichroic mirror 55, which construct the first optical system 51 are two-dimensionally laid out in the region 58 that extends in two dimensions on the first frame 50, and the holders 83 to 89 of these components are also laid out in two dimensions. Accordingly, by constructing the emission block 11 of the first frame 50 and the light shielding cover (not illustrated) that covers the storage region 58, it is possible to adjust the respective positions of the optical elements extremely easily by merely removing the cover. In addition, the positions of the respective optical axes in the XY directions can be adjusted by the XY tables 82a and 82b provided on the outside of the wall surfaces of the first frame 50. In the emission block 11, it is also possible to finely adjust the positions of the built-in optical elements independently and separately to the other blocks 12 and 14 so that the pump light 5 and the Stokes light 6 are concentrated at the focusing position (first point) 2a that is set in advance. By attaching the adjusted emission block 11 to the frame 13f of the shared base 13, it is possible to achieve a predetermined performance as the optical head 10.

The second frame 60 that constructs the collection block 12, which is attached to the shared frame 13f on the other side of the sample holding block 14 to the emission block 11, is a pentagonal box shape in the form of like a right trapezoid when viewed from above. The second frame 60 internally includes a storage region 68 that extends in two dimensions and is surrounded by five walls 67a to 67e. Out of the side walls of the second frame 60, the side wall 67a that faces the sample holding block 14 is provided with a window (opening, aperture) 67x for collecting the CARS light 7 emitted from the cuvette 2, and the side wall 67b adjacent to the side wall 67a has a connector 65 for the optical fiber 35 that guides the CARS light 7 fixed thereto. Accordingly, two walls 67a and 67b of the five side walls 67a to 67e of the second frame 60 that is in the form of like a right trapezoid are used for inputting and outputting light, and the remaining side walls 67c to 67e are walls that face the side walls of the housing 40 when the collection block 12 is housed in the housing 40 and shield the inside of the collection block 12.

With the collection block 12 provided with the second frame 60 which is in the overall shape of like a right trapezoid, the side wall 67d that is inclined so as to form the right trapezoid is shaped so as to facilitate housing inside a corner where the housing 40 tends to be curved or have increased thickness. At the same time, by disposing a bending mirror 66 on the inclined side wall 67d, the optical path for guiding the CARS light 7 to the optical fiber 35 is bent inside the collection block 12, which makes it possible to compactly arrange the plurality of optical elements included in the second optical system 61.

A window 67x and an objective lens 62 for collecting the CARS light 7, a filter 63, a collimator lens 64 for concentrating the CARS light 7, and a connector 65 for outputting the CARS light 7 are disposed in the region 68 that extends in two dimensions inside the second frame 60 so as to form two optical paths that are perpendicular to the bending mirror 66 disposed in the corner.

The collection block 12 also includes mechanisms that finely adjust and then fix the attachment positions of the respective optical elements of the second optical system 61 disposed on the inside of the second frame 60 and the wall surface 67 to the second frame 60, with the storage region 68 that extends in two dimensions inside the second frame 60 as a base. In more detail, the collection block 12 includes: a third XY table (third XY position adjustment unit) 95 that finely adjusts and then fixes the position relative to the second frame 60, in the present embodiment, the side wall 67b, of the third connector 65, which guides the CARS light 7 to the optical fiber, in two dimensions that are perpendicular to the optical axis 7x of the CARS light 7; and a holder (focus adjustment unit) 92 that finely adjusts and then fixes the position relative to the second frame 60 of the second objective lens 62 in the direction of the optical axis 7x of the CARS light 7. The collection block 12 may also include a holder 94 which supports the collimator lens 64 so as to be slidable relative to the second frame 60 and finely adjusts and then fixes the attachment position along the optical axis 7x. As the holders 92 and 94, it is possible to use the same mechanism as the holder (focus adjustment unit) 89 described above. It is also possible to use the fine adjustment table 100 described earlier as the third XY table 95.

The collection block 12 may further include a holder 93 that slidably supports the attachment position of the filter 63 relative to the second frame 60 and finely adjusts and then fixes the attachment position, a holder 96 that finely adjusts and then fixes the attachment position and angle of the mirror 66, and a holder 92 that adjusts and then fixes the attachment position of the objective lens 62.

By adjusting the position of the optical axis 7x of the objective lens 62 that has positive refractive power using the holder 92, it is possible to cope with variations in the emission position of the CARS light 7. In the present embodiment, the objective lens 62 can be moved about 5 mm backward and forward using the holder 92, so that it is possible to move the point at which the CARS light 7 can be collected in the thickness direction of the cuvette (sample cell) 2. By finely adjusting the position of the collimator lens 64, which has overall positive power and includes the biconvex positive lens 64a and the negative meniscus lens 64b that is convex on the emission side and is cemented to the positive lens 64a, using the holder 94, it is possible to cope with a spreading of light flux due to movement of the objective lens 62, and possible to efficiently guide the CARS light 7 to the fiber 35. In addition, using the third XY table 95, it is possible to finely adjust the position in the XY directions at which the CARS light 7 is guided to the optical fiber. Accordingly, the optical path of the CARS light 7 in the collection block 12 can be controlled in all of the XY directions, which are perpendicular to the optical axis 7x, and the Z direction, which is parallel to the optical axis 7x. This makes it possible to efficiently gather the CARS light 7 outputted from the cuvette 2 and guide the CARS light 7 to the optical fiber 35.

In the collection block 12 also, the lenses 62 and 64, the filter 63, and the mirror 66 described above that compose the second optical system 61 and also their holders 92 to 96 are laid out in the region 68 that extends in two dimensions in the second frame 60. Accordingly, in the same way as the emission block 11, by constructing the collection block 12 of the second frame 60 and a light shielding cover (not illustrated) that covers the storage region 68, it is possible to adjust the respective positions of the optical elements extremely easily by removing the cover.

In the collection block 12 also, by finely adjusting the positions of these built-in optical elements independently and separately from the other blocks 11 and 14 so as to efficiently collect the CARS light 7 from the generation point (first point) 2a of the CARS light 7, which is set in advance, and then attaching the collection block 12 to the shared base 13, it is possible to achieve a predetermined performance as the optical head 10. Although the optical head 10 according to the present embodiment has the emission block 11 and the collection block 12 linearly disposed using the shared base 13 with the sample holding block 14 in between, it is also possible to provide an optical head 10 that uses a base 13 where the emission block 11 and the collection block 12 are disposed diagonally or at an angle and that collects CARS light 7 outputted diagonally or at an angle from the sample or CARS light 7 outputted from the skin or subcutaneous tissue, such as a blood vessel.

Figure 5A:
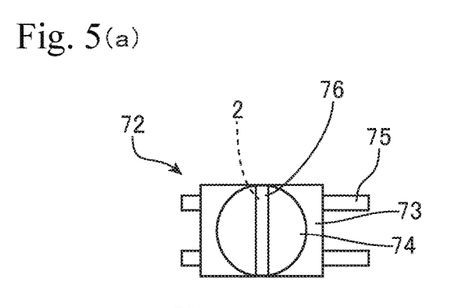
FIGS. 5(a)-5(e) is a diagram useful in explaining the configuration of a sample holder.
Figure 5B:
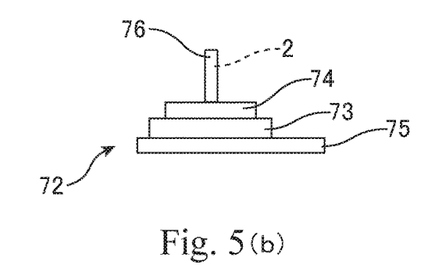

The sample holding block 14 includes a high rigidity fourth frame 70 that is attached to the high rigidity frame 13f of the shared base 13 and a sample holder 72 that fixes the cuvette (sample cell) 2 containing a sample to the fourth frame 70. As depicted in FIGS. 5(a) and (b), the sample holder 72 includes a first stage 73 that uses rails 75 to move the position of the cuvette 2 relative to the fourth frame 70 in parallel with the optical axis with the irradiation light (emitted light) 8 including the pump light 5 and the Stokes light 6, a second stage 74 that rotates relative to the optical axis of the emitted light 8 on the first stage 73, and a cuvette holder 76 that holds the cuvette 2 on the second stage 74 in a predetermined posture. The position (in the depth direction) of the point 2a at which the pump light 5 and the Stokes light 6 are concentrated to generate the CARS light 7 in the sample, such as blood, stored or kept in the cuvette 2 and the angle at which the generated CARS light 7 is collected by the detector 30 via the collection block 12 can be freely adjusted by these stages 73 and 74.

Figures 5C, 5D, 5E:
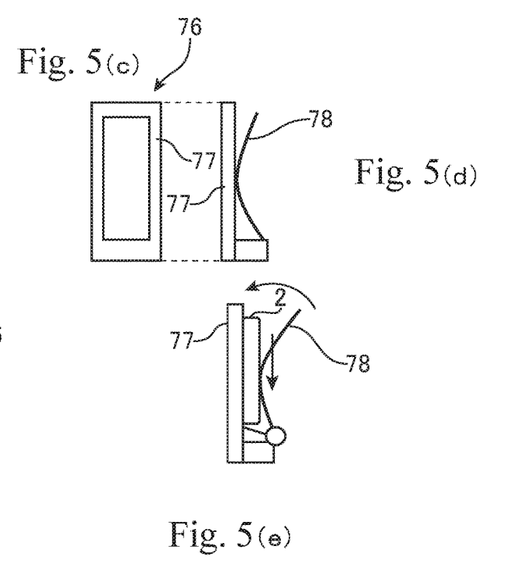

As depicted in FIGS. 5(c), 5(d), and 5(e), the cuvette holder 76 includes a support portion 77 that is highly rigid and whose position along the optical axis of the emitted light 8 is a transmission window and a plate spring 78 that elastically presses and holds the cuvette 2 against the support portion 77. This configuration of the cuvette holder 76 is merely one example, and any design capable of holding the cuvette 2 on the stage 74 of the sample holder 72 in a fixed posture may be used.

As described above, the measuring apparatus 1 according to the present embodiment includes the optical head 10, which is compact but includes the emission block (first module) 11, the collection block (second module) 12, and the third module 13 including the shared frame 13f that fixes the positions of the blocks 11 and 12, and the optics of the blocks 11 and 12 can be separately subjected to fine adjustment. Accordingly, it is possible to stably and accurately collect the CARS light 7 with the handy-sized measuring apparatus 1, and possible to perform measurement and analysis using Raman spectroscopy, in particular, the CARS light 7. Although it is also possible to use this optical head 10 to obtain spontaneous Raman scattered light instead of the CARS light 7, for purposes such as trace analysis of blood components, like glucose concentration in the blood, and acquiring three-dimensional images of cells in the blood, it is desirable to acquire the CARS light 7.

Figure 6A:
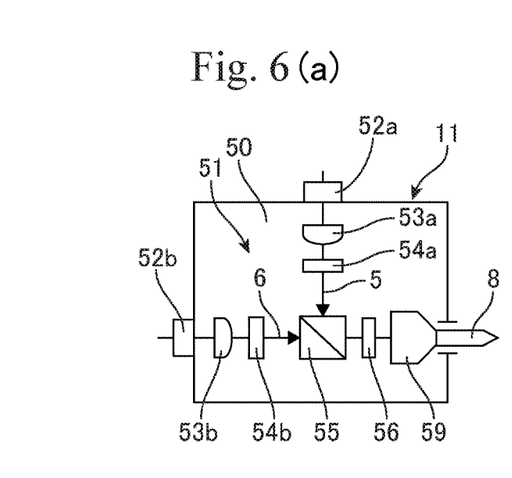
FIGS. 6(a)-6(e) is a diagram depicting another example of an emission block.

Some example configurations of the emission block 11 are depicted in FIGS. 6(a)-6(e). FIG. 6(a) shows a schematic configuration of the emission block 11 that combines the pump light 5 and the Stokes light 6 using the dichroic prism 55. The emission block 11a shown in FIG. 6(b) has a configuration in which the input angle between the pump light 5 and the Stokes light 6 is kept at 90 degrees by a combination of a mirror 121 and a notch filter 120. In the emission block 11a, the pump light 5 and the Stokes light 6 are combined by the notch filter 120 or a dichroic mirror that transmits the wavelength band of the Stokes light 6 and reflects the wavelength band of the pump light 5. Since the reflection angle at the notch filter 120 can be reduced compared to a configuration that uses the dichroic prism 55, the reflection efficiency becomes higher. In addition, since it is possible to use the notch filter 120 that has high reflection efficiency, this configuration has low attenuation of the laser beam during combining, which makes it easy to achieve a sufficient irradiation intensity.

Figure 6B:
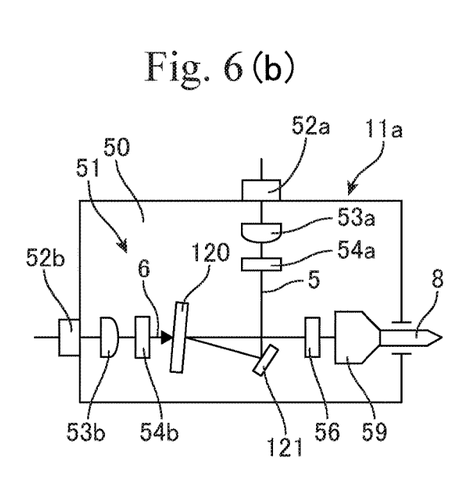
Figure 6C:
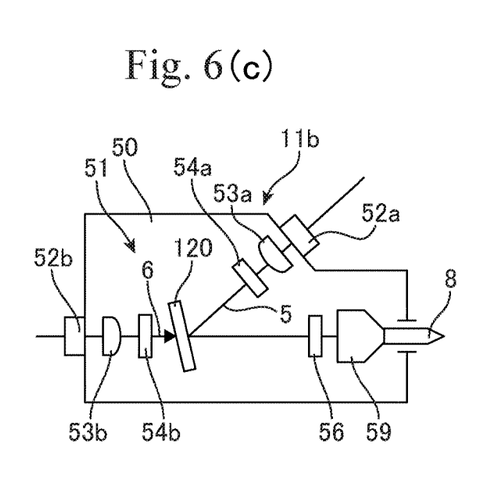
Figure 6D:
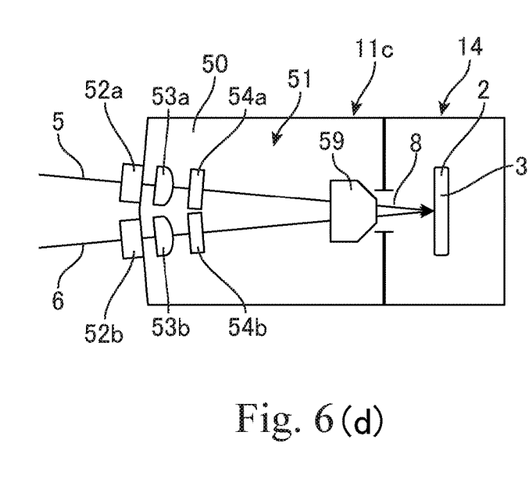
Figure 6E:
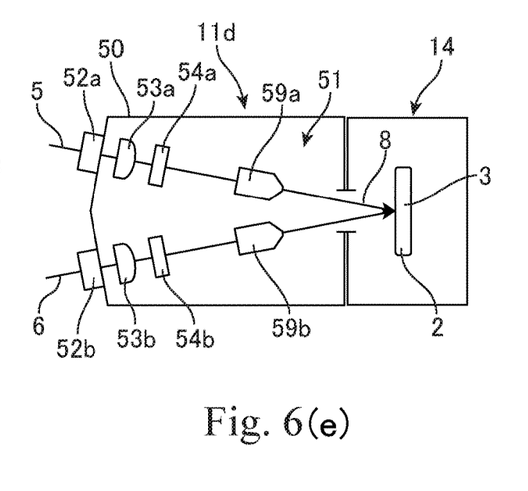

The emission block 11b depicted in FIG. 6(c) includes a configuration in which the pump light 5 and the Stokes light 6 can be combined by the notch filter 120 or a dichroic mirror without using a reflective mirror. By omitting a reflective mirror, it is possible to further suppress attenuation of laser beam. The emission block 11c shown in FIG. 6(d) includes a configuration in which the pump light 5 and the Stokes light 6 are separately inputted to the objective lens 59 used for focusing and are combined by the objective lens 59. One of the beams may be guided via a number of mirrors. The emission block 11d depicted in FIG. 6(e) includes a configuration in which the pump light 5 and the Stokes light 6 are concentrated on the sample 3 (the cuvette 2) via different objective lenses 59a and 59b. In the emission block 11d, a configuration can be used where chromatic aberration is reduced by concentrating the Stokes light 6 that has a wide wavelength band using a parabolic mirror.

With an emission block of any of these types, the aberration correcting performance can be improved by using aspherical lenses for the collimator lenses 53a and 53b and the objective lens 59. In particular, chromatic aberration can be improved by using aspherical lenses for the collimator lens 53b and the objective lens 59 that pass the Stokes light 6, which has a wide wavelength band.

Figure 7:
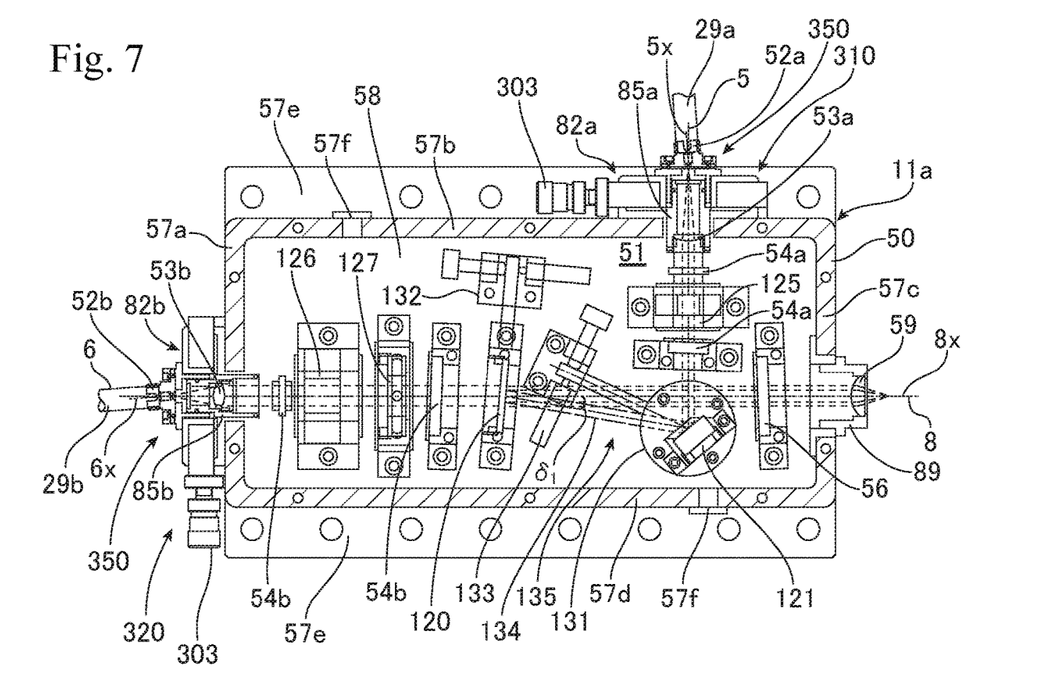
FIG. 7 is a plan view depicting the internal layout of another example of an emission block.
Figure 8:
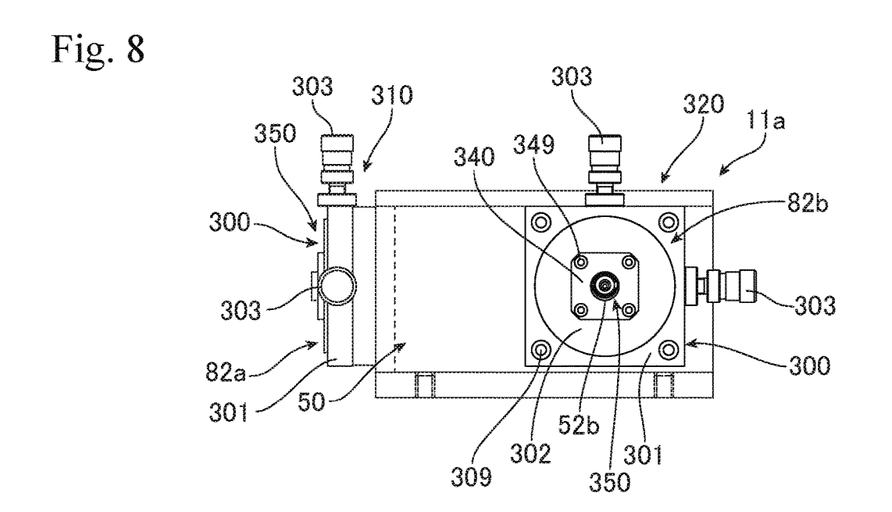
FIG. 8 is a side view of the emission block shown in FIG. 7.

FIG. 7 depicts a more specific example configuration of the emission block 11a of the type depicted in FIG. 6(b). FIG. 8 depicts the configuration when looking from the side of the emission block 11a. The emission block 11a also has the highly rigid first frame (first housing) 50 in which the optical elements of the first optical system 51 depicted in FIG. 6(b) are housed. In the illustrated example, the reflection angle 61 at the notch filter 120 is around 10 degrees, but the reflection angle δ1 may be around 5 to 20 degrees or around 5 to 15 degrees.

In addition, since a CARS signal is always generated with a non-resonant portion, it is desirable to reduce the intensity of the non-resonant portion in order to improve the measurement accuracy. Several methods have been proposed for this purpose, and time-resolved CARS (T-CARS) and polarization-sensitive CARS (P-CARS) can be given as examples. The emission block 11a depicted in FIG. 7 is for polarization-sensitive CARS, so that the cuvette 2 is irradiated via the objective lens 59 after polarization elements are inserted onto the optical paths of the pump light 5 and the Stokes light 6 to control the polarization directions.

The emission block 11a includes a first laser light supplying module (first laser beam supplying module) 310 that introduces the pump light 5 into the first housing 50 from the optical fiber 29a and a second laser light supplying module (second laser light supplying module) 320 that introduces the Stokes light 6 into the first housing 50 from the optical fiber 29b. The first laser light supplying module 310 includes an input module 350 including the first connector 52a and the first XY table 82a that adjusts the position in the XY directions, which are perpendicular to the optical axis 5x, of the input module 350 relative to the first housing 50. The second laser light supplying module 320 includes an input module 350 including the second connector 52b and a second XY table 82b that adjusts the position in the XY directions, which are perpendicular to the optical axis 6x, of the input module 350 relative to the first housing 50. The first laser beam supplying module 310 includes a holder 85a that finely adjusts the position (Z position) along the optical axis 5x of the first collimator lens 53a and the second laser beam supplying module 320 includes a holder 85b that finely adjusts the position (Z position) along the optical axis 6x of the second collimator lens 53b. The laser light supplying modules 310 and 320 will be described in more detail later.

The first optical system 51 mounted on the emission block 11a includes the first collimator lens 53a, the band pass filter 54a, a polarizing element 125, a band pass filter 54a, and a mirror 121 for reflecting the pump light 5 in the direction of the notch filter 120, which are disposed along the incident direction of the pump light 5. The first optical system 51 also includes the second collimator lens 53b, the long wavelength pass filter 54b, a polarization element 126, a half wave plate 127, the filter 54b, and the notch filter 120, which are disposed along the incident direction of the Stokes light 6. The Stokes light 6 that has passed through the notch filter 120 is combined with the pump light 5 and coaxially introduced into the objective lens 59. The emission block 11a includes a holder 89 that finely adjusts the position along the optical axis 8x of the objective lens 59, and can precisely control the focal positions of the pump light 5 and the Stokes light 6.

The emission block 11a further includes an adjustment unit 132 that finely adjusts the position along the optical axis 6x of the notch filter 120, an adjustment unit 133 that finely adjusts the rotation angle of the mirror 121, and a link mechanism 135 for coordinated control of the position of the notch filter 120 and the rotation angle of the mirror 121. The link mechanism 135 includes a link lever 134 that extends along an optical axis which connects the notch filter 120 and the mirror 121, and a rotation mechanism 131 that rotates the mirror 121. When the notch filter 120 for adjusting the optical path is moved along the optical axis 6x, the rotation mechanism 131 rotates the mirror 121 by an angle that is half of the angle about which the link lever 134 pivots due to the movement of the notch filter 120.

Figure 9:
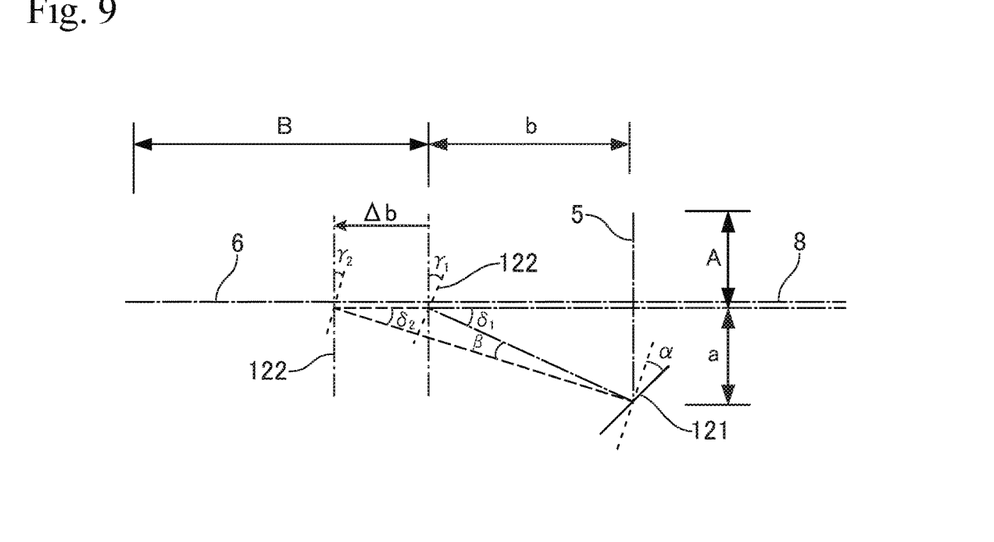
FIG. 9 is a diagram for explaining a difference in optical paths.

As depicted in FIG. 9, when the notch filter 120 moves by Δb to synchronize the pump light 5 and the Stokes light 6 supplied as pulse signals, the optical path length Lp of the pump light 5 and the optical path length Ls of the Stokes light 6 change as indicated below.

$$Lp = A + a + (a^2 + (b + \Delta b)^2)^{1/2}$$

$$Ls = B - \Delta b$$

Since the rotation angle α of the mirror 121 is double the change β in the reflection angle of the pump light 5, by having the link mechanism 135 automatically rotate the mirror 121 in keeping with movement of the notch filter 120, synchronous adjustment of the pump light 5 and the Stokes light 6 in the block 11a becomes easy.

The first frame 50 that supports and houses the optical system 51 of the emission block 11a is substantially rectangular and includes the four side walls 57a to 57d, and includes an overhanging portion 57e of the base plate 58 for further improving rigidity. Holes 57f for supplying and discharging air are provided at appropriate positions on the side walls 57a to 57d, so that the inside which is surrounded by the first frame 50 where the optical system 51 is installed can be ventilated to suppress changes in temperature and humidity.

Figure 10A:
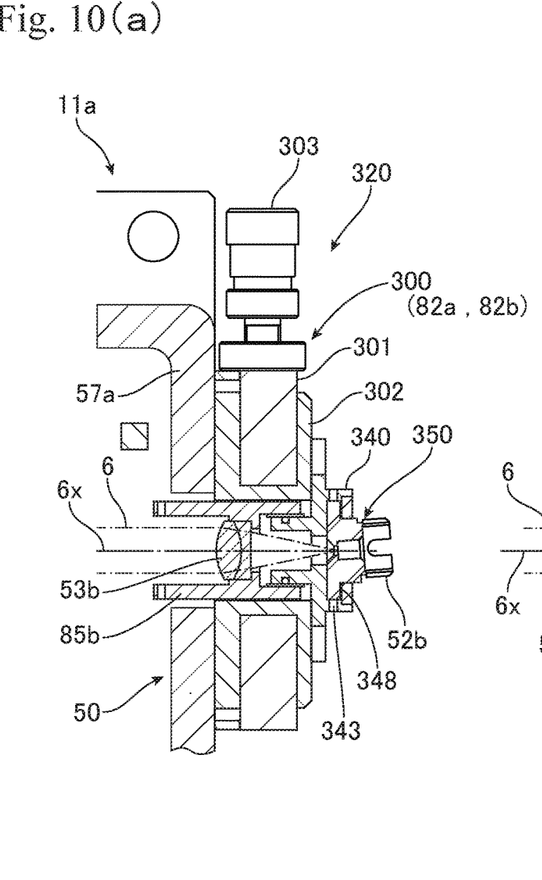
FIG. 10(a) is a cross-sectional view depicting the overall construction of a laser light supplying module and FIG. 10(b) schematically depicts the configuration of the laser light supplying module.
Figure 10B:
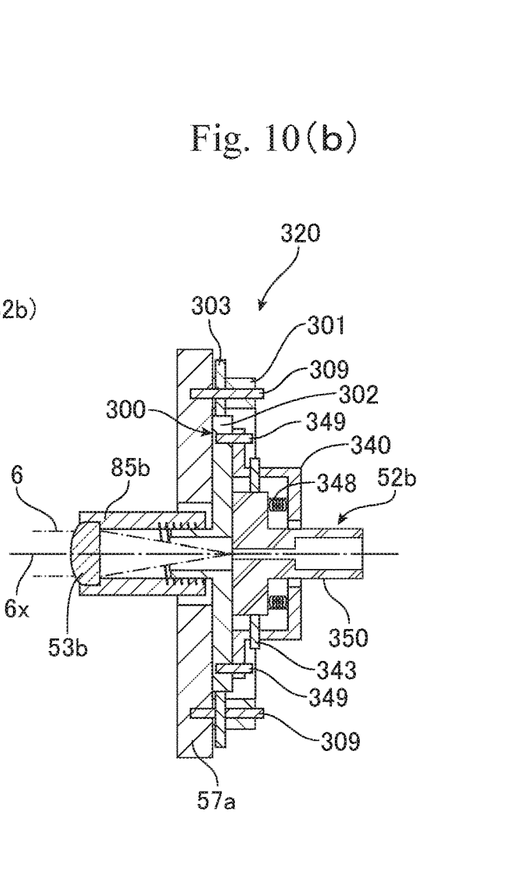

FIGS. 10(a) and 10(b) depicts the second laser light supplying module (laser beam supplying module) 320, which supplies the Stokes light 6. The first laser light supplying module 310 that supplies the pump light 5 also has the same configuration. FIG. 10(a) depicts a specific configuration of the laser supply module 320 used in the present embodiment, and FIG. 10(b) is a schematic diagram depicting a conceptual configuration of the laser supply module 320.

The laser beam supplying module 320 includes an XY table 300 with a shared configuration that functions as the first XY table 82a and the second XY table 82b and an input module 350 that is attached so that the position in directions (XY directions) perpendicular to the optical axis 6x relative to the XY table 300 can be adjusted. On the XY table 300, the position in the XY directions of the inner frame 302, to which the input module 350 is fixed, is fixed after being finely adjusted relative to the outer frame 301 by a micrometer-type fine adjustment screw 303 attached to the outer frame 301. The outer frame 301 is fixed to the side wall 57a of the first frame 50 by the screws 309, the inner frame 302 moves along the side wall 57a, and the position relative to the first frame 50 is adjusted by the fine adjustment screw 303.

The second collimator lens 53b is attached via a holder 85b to the inner frame 302 of the XY table 300. Accordingly, after the positions (Z positions) along the optical axis 6x of the input module 350, which includes the second connector 52*b*, and the second collimator lens 53*b* have been adjusted in the laser light supplying module 320, then the laser light supplying module 320 is attached via the XY table 300 to the first frame 50, and its position relative to the first frame 50 is finely adjusted integrally with the input module 350 by the XY table 300.

The laser light supplying module 320 further includes a unit (cover) 340 that attaches the input module 350 to the inner frame 302 in a state where the position of the input module 350 can be adjusted in the XY directions. The cover 340 is fixed to the inner frame 302 by screws 349 so as to cover at least part of the input module 350. The cover 340 includes a spring (elastic body) 348 for pressing the internal input module 350 against the inner frame 302 and adjustment screws (grub screws) 343 that finely adjust the position of the input module 350 in the XY directions (that are perpendicular to the optical axis 6*x*) relative to the inner frame 302. Accordingly, in the laser light supplying module 320, the position, relative to the second collimator lens 53*b* that is fixed to the inner frame 302, in the XY directions of the connector 52*b* where the Stokes light (laser light) 6 is incident can be finely adjusted for the laser light supplying module 320 by itself. The input module 350 is pressed against the inner frame 302 by the spring 348, moves in the XY directions in close contact with the spring 348, and the inner frame 302 moves in the XY directions while in close contact with the surface of the side wall 57*a* of the frame 50. This means that the positions of the collimator lens 53*b* in the XY directions and the Z direction can be precisely adjusted with the frame 50 as a standard.

The positions of the connector 52*b* and the collimator lens 53*b* in the XY directions and the Z direction can be decided for the laser beam supply module 320 by itself, that is, in a state where the laser beam supply module 320 has been removed. This means that before attaching the laser light supplying module 320 to the frame 50, it is possible to adjust the collimation of the laser light (beams) of the pump light 5 and the Stokes light 6 using a dedicated jig.

Figure 11:
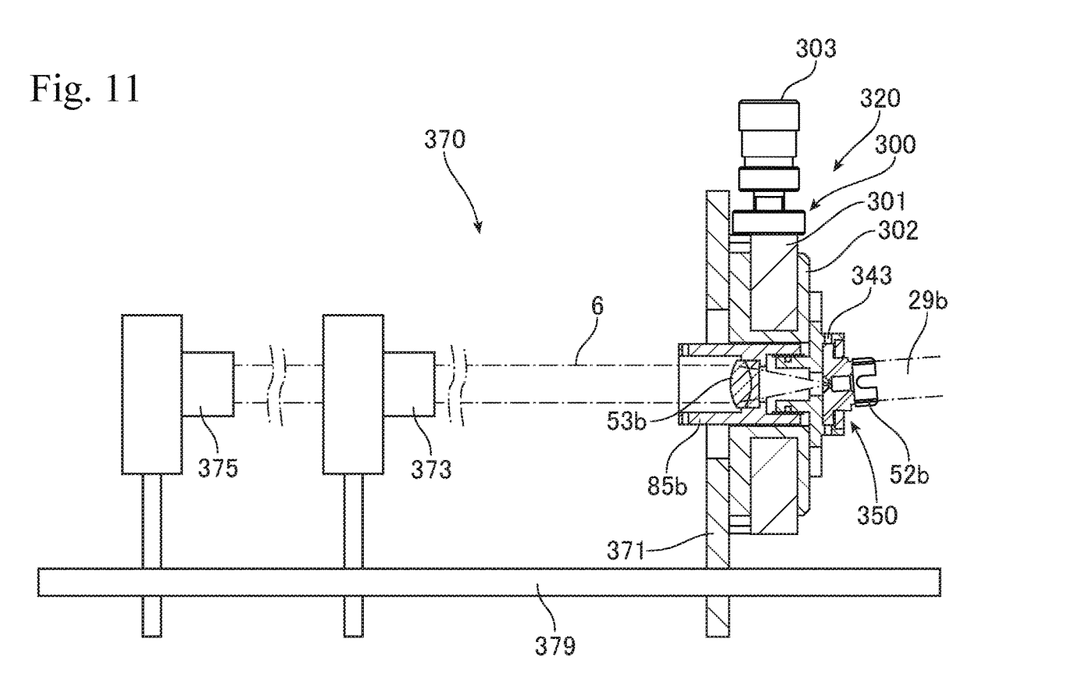
FIG. 11 depicts one example of a dedicated jig for adjusting collimation.

FIG. 11 depicts an example of a dedicated jig (special equipment) for adjusting collimation. The dedicated jig 370 includes a frame 371 that fixes the laser beam supplying module 320 to an optical base plate 379, a first beam profiler 373 set at a first position sufficiently far from the frame 371, and a second beam profiler 375 set at a second position that is further away. The XY position of the input module 350 relative to the inner frame 302 that serves as a base is adjusted by the grub screws 343 of the cover 340 and the Z position of the collimator lens 53*b* is adjusted by the holder 85*b* so that the laser beam supplying module 320 set in the dedicated jig 370 has the same beam diameter in the first beam profiler 373 and the second beam profiler 375. By performing these adjustments, the XY positions and the Z positions of the collimator lens 53*b* and the connector 52*b* in the laser light supplying module (laser beam supplying module) 320 are respectively decided in a state in which parallel light beams are obtained. Accordingly, after this, the position of the inner frame 302 relative to the frame 50 is adjusted by the XY table 300 in a fixed state, without moving the position of the collimator lens 53*b* and the position of the input module 350 relative to the inner frame 302, thereby adjusting the relationship with the other optical elements of the optical system 51 housed in the frame 50. As the beam profilers 373 and 375, beam meters, target plates, laser viewers using phosphors or fluorescent materials, or the like may be used.

The emission block 11*a* depicted in FIG. 7 can construct the optical head 10 by being fixed to the supporting block 13 together with the collection block 12. The sample holding block 14 may also be fixed to the supporting block 13. In the optical head 10, the positions of the connectors 52*a* and 52*b* in the XY and Z directions relative to the collimator lenses 53*a* and 53*b* are adjusted in units of the laser beam supplying modules 310 and 320 then fixed to the first frame 50. In addition, the positions of the respective optical elements in the first optical system 51 are adjusted in units of the emission block 11*a* then fixed to the first frame 50. Similarly, in the collection block 12, the positions of the optical elements of the second optical system 61 are adjusted in units of the collection block 12 and fixed to the second frame 60. In addition, by fixing the first frame 50 and the second frame 60 to the shared frame 13*f*, it is possible to precisely set and fix the optical elements that construct the optical head 10 relative to the frame 13*f* and it is possible to provide an optical head 10 that is suited to measuring nonlinear Raman spectral effects such as CARS or SRS.

Although the measuring apparatus 1 according to the embodiment described above uses two laser units to obtain the pump light (pump beam) 5 and the Stokes light (Stokes beam) 6, it is also possible to split the output of a single laser unit into the pump beam 5 and the Stokes beam 6 using a beam separator or the like. Also, although broadband SC light is used as the Stokes light 6, it is also possible to use a tunable laser whose wavelength can be controlled. When a tunable laser is used, instead of a spectral type, a light detection device that measures only light intensity may be used as the detector 30. By measuring the intensity of the CARS light relative to the wavelength of the Stokes light, it is possible to obtain the spectrum of the CARS light as a result.

Also, with the measuring apparatus 1 according to the present embodiment, although a laser light source is provided separately to the optical head 10 in order to obtain a high energy laser, it is also possible to incorporate a small laser light source, such as a semiconductor laser or a microchip laser, in the optical head 10. That is, the emission block 11 may include a laser element that outputs the pump light 5 in place of the first connector 52*a* as the first laser light supplying unit, and a laser element that outputs Stokes light 6 in place of the connector 52*b* as the second laser light supplying unit. These laser elements may be tunable lasers. It is also desirable for the supplying units including these laser elements to be adjustable in directions (XY directions) perpendicular to their respective optical axes.

It is also possible for the optical head 10 to house a detector that detects the CARS light 7 as a light receiving unit in place of the third connector 65. As one example, the collection block 12 may house a light detection device, such as a CCD, that is compatible with a tunable laser. It is desirable for the detector also to be adjustable in the directions (XY directions) perpendicular to the optical axis. By providing an optical head that houses a laser source, it is possible to provide a more compact measuring apparatus, and as one example, to provide a measuring apparatus that can be used as a wearable Raman analyzer that continuously measures blood sugar level or the like.

Although the emission block 11, the sample holding block 14, and the collection block 12 are fixed in a linear arrangement using the shared base 13 in the optical head 10 of the measuring apparatus 1 according to the present embodiment, it is also possible to omit the sample holding block 14. As one example, in order to obtain CARS light from the skin or subcutaneous tissue, it is also possible to fix the emission block 11 and the collection block 12 to the shared base 13 so that the emission block 11 and the collection block 12 are disposed facing the skin or the like to be measured.

Figure 12:
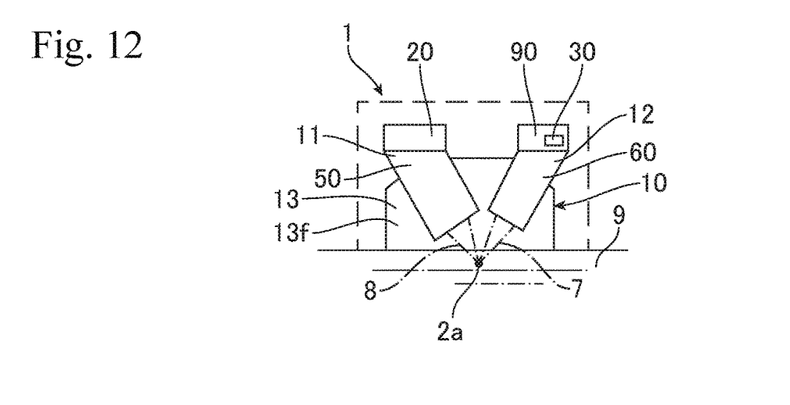
FIG. 12 depicts another example of a measuring apparatus.

FIG. 12 depicts an example of a measuring apparatus 1 used to collect the CARS light 7 to be measured, with subcutaneous tissue or a capillary of the skin 9 as the irradiation point (first point) 2*a*. In the optical head 10 of this measuring apparatus 1, the first frame 50 that constructs the emission block 11 is fixed to the shared frame 13*f* so as to emit the irradiation beam 8 produced by combining the pump light 5 and the Stokes light 6 onto a predetermined point 2*a* in the subcutaneous tissue and the collection block 12 is fixed to the shared frame 13*f* so as to collect the CARS light 7 emitted from the irradiated point. The measuring apparatus 1 may be equipped with a laser unit 20, and may be equipped with an analysis unit 90 including the spectrometer 30. The measuring apparatus 1 may be an information acquiring apparatus that acquires biological information including a blood sugar level or the like using the analysis unit 90 and transmits the information to the user or via the cloud to a facility that performs monitoring, such as a medical facility.

The optical head 10 is not limited to the pump light 5 and the Stokes light 6 but may combine light inputted with other frequencies or frequency bands or other timing, for example, probe light, for measuring nonlinear Raman spectral scattering. The optical head 10 may irradiate the first point 2*a* with light (laser beam) for acquiring information by other spectroscopy or another optical analysis method simultaneously or in parallel with nonlinear Raman spectroscopy. Optical coherence tomography (OCT), fluorometry, and laser induced breakdown spectrometry (LIBS) can be given as examples of other optical analysis methods.

The invention claimed is:

1. An optical head comprising:
   an emission block that includes a high rigidity first frame and a first optical system including a plurality of optical elements fixed to the first frame to concentrate a plurality of light of different frequencies or frequency bands on a first point to obtain a nonlinear Raman effect;
   a collection block that includes a high rigidity second frame and a second optical system including a plurality of optical elements fixed to the second frame to collect light to be measured emitted from the first point; and
   a supporting block that includes a high rigidity third frame, the first frame and the second frame being fixed on the third frame to support the first optical system and the second optical system precisely positioned each other to the first point.

2. The optical head according to claim 1,
   wherein the emission block includes a mechanism that adjusts and then fixes an attachment position of at least one optical element included in the first optical system to the first frame, and
   the collection block includes a mechanism that adjusts and then fixes an attachment position of at least one optical element included in the second optical system to the second frame.

3. The optical head according to claim 1,
   wherein the first frame includes a region that extends in two dimensions and the plurality of optical elements included in the first optical system are laid out in two dimensions in the first frame.

4. The optical head according to claim 1,
   wherein the second frame includes a region that extends in two dimensions and the plurality of optical elements included in the second optical system are laid out in two dimensions in the second frame.

5. The optical head according to claim 1,
   further comprising a first laser light supplying source and a second laser light supplying source that are fixed to the first frame and each supply at least one of the plurality of light,
   wherein the plurality of optical elements of the first optical system include a plurality of optical elements that construct an optical path that guides first laser light supplied from the first laser light supplying source and second laser light supplied from the second laser light supplying source to a shared first objective lens that irradiates the first point,
   and the optical head further comprises:
   a first XY table that adjusts a position in two dimensions perpendicular to an optical axis of the first laser light, of the first laser light supplying source relative to the first frame; and
   a second XY table that adjusts a position in two dimensions perpendicular to an optical axis of the second laser light, of the second laser light supplying source relative to the first frame.

6. The optical head according to claim 5,
   further comprising:
   a first collimator lens that converts the first laser light to parallel light;
   a second collimator lens that converts the second laser light to parallel light;
   a first holder that holds the first collimator lens and adjusts a position, in an optical axis direction of the first laser light, of the first collimator lens relative to the first frame; and
   a second holder that holds the second collimator lens and adjusts a position in an optical axis direction of the second laser light, of the second collimator lens relative to the first frame.

7. The optical head according to claim 6,
   wherein the first holder is fixed to the first frame together with the first laser light supplying source via the first XY table, and
   the second holder is fixed to the first frame together with the second laser light supplying source via the second XY table.

8. The optical head according to claim 7,
   further comprising:
   a first cover that attaches with the first laser light supplying source to adjust a position in two dimensions, which are perpendicular to the optical axis of the first laser light, relative to the first collimator lens, and
   a second cover that attaches with the second laser light supplying source to adjust a position in two dimensions, which are perpendicular to the optical axis of the second laser light, relative to the second collimator lens.

9. The optical head according to claim 5,
   wherein the first laser light supplying source includes a laser element that supplies the first laser light or a first connector that connects to an optical fiber that supplies the first laser light, and
   the second laser light supplying source includes a laser element that supplies the second laser light or a second connector that connects to an optical fiber that supplies the second laser light.

10. The optical head according to claim 5,
further comprising a holder that adjusts a position in an optical axis direction of the first objective lens relative to the first frame.

11. The optical head according to claim 1,
further comprising a sample holding block that includes a high rigidity fourth frame that is fixed to the third frame and a sample holder that is fixed to the fourth frame to fix a sample at the first point.

12. The optical head according to claim 11,
wherein the sample holding block includes a mechanism that adjusts and then fixes an orientation of the sample holder.

13. The optical head according to claim 1,
wherein the plurality of optical elements of the second optical system include a plurality of optical elements that construct an optical path from a second objective lens that concentrates the light to be measured, to a light receiver that receives the light to be measured.

14. The optical head according to claim 13,
further comprising:
a third XY table that adjusts a position in two dimensions perpendicular to an optical axis of the light to be measured, of the light receiver relative to the second frame; and
a holder that adjusts a position, in an optical axis direction of the light to be measured, of the second objective lens relative to the second frame.

15. The optical head according to claim 13,
wherein the light receiver includes a detector that detects the light to be measured or a third connector that connects to a third optical fiber that guides the light to be measured to a detector.

16. The optical head according to claim 13,
wherein the light receiver includes a detector that detects the light to be measured and a third connector that connects to a third optical fiber that guides the light to be measured to a detector.

17. The optical head according to claim 1,
wherein the light to be measured includes light that has been generated due to at least one of stimulated Raman scattering and coherent anti-Stokes Raman scattering.

18. A measuring apparatus comprising:
the optical head according to claim 1;
a light source that outputs the plurality of light; and
a detector that detects the light to be measured.

* * * * *